(12) United States Patent
Hsieh et al.

(10) Patent No.: US 8,088,838 B2
(45) Date of Patent: Jan. 3, 2012

(54) CONE MATERIAL IN ENDODONTIC TREATMENT

(75) Inventors: Kuo-Huang Hsieh, Taipei (TW);
Chun-Pin Lin, Taipei (TW);
Ken-Hsuan Liao, Taipei (TW);
Chung-Yi Lee, Taipei (TW);
Ching-Ting Tsao, Taipei (TW)

(73) Assignee: National Taiwan University, Taipei (TW)

( * ) Notice: Subject to any disclaimer, the term of this patent is extended or adjusted under 35 U.S.C. 154(b) by 287 days.

(21) Appl. No.: 12/393,192

(22) Filed: Feb. 26, 2009

(65) Prior Publication Data
US 2009/0156710 A1 Jun. 18, 2009

Related U.S. Application Data

(63) Continuation-in-part of application No. 11/765,575, filed on Jun. 20, 2007, now abandoned.

(51) Int. Cl.
| | |
|---|---|
| A61L 24/02 | (2006.01) |
| A61K 6/09 | (2006.01) |
| A61K 6/087 | (2006.01) |
| A61C 5/00 | (2006.01) |
| A61C 5/02 | (2006.01) |
| A61C 5/04 | (2006.01) |
| C08G 18/42 | (2006.01) |
| C08L 75/06 | (2006.01) |

(52) U.S. Cl. ........ 523/116; 523/113; 523/115; 433/224; 433/226; 433/228.1; 106/35; 524/590; 525/453

(58) Field of Classification Search .................. 523/116, 523/113, 115; 433/224, 226, 228.1; 160/35; 524/590; 525/453
See application file for complete search history.

(56) References Cited

U.S. PATENT DOCUMENTS

| | | | | |
|---|---|---|---|---|
| 5,263,861 | A * | 11/1993 | Cohen et al. | 433/224 |
| 6,353,041 | B1 * | 3/2002 | Qian | 523/116 |
| 2005/0027033 | A1 * | 2/2005 | Knaack et al. | 523/115 |
| 2005/0107562 | A1 * | 5/2005 | Leberfinger et al. | 528/44 |

OTHER PUBLICATIONS

Kuo-Huang Hsieh, Ken-Hsuan Liao, Eddie Hsiang-Hua Lai, Bor-Shiunn Lee, Chung-Yi Lee, and Chun-Pin Lin; A Novel Polyurethane-based Root Canal-obturation Material and Urethane Acrylate-based Root Canal Sealer—Part I: Synthesis and Evaluation of Mechanical and Thermal Properties; Basic Research—Technology; Joe- vol. 34, No. 3, Mar. 2008; ZNO Root Cannal-Obturation Material and UA/TPGDA Root Canal Sealer; p. 303-305.

Bor-Shiunn Lee, Eddie Hsiang-Hua Lai, Ken-Hsuan Liao, Chung-Yi Lee, Kuo-Huang Hsieh, and Chun-Pin Lin; A Novel Polyurethane-based Root Canal-obturation Material and Urethane-Acrylate-based Root Canal Sealer—Part 2: Evaluation of Push-out Bond Strengths; Basic Research—Technology; Joe-vol. 34, No. 5, May 2008; p. 594-598.

* cited by examiner

*Primary Examiner* — Michael Pepitone
(74) *Attorney, Agent, or Firm* — WPAT., P.C.; Justin King

(57) ABSTRACT

The present invention discloses a cone material in endodontic treatment. The cone material comprises a thermoplastic polyurethane and a filler. The thermoplastic polyurethane is formed by a. isophorone diisocyanate (IPDI) or hexamethylene diisocyanate (HDI), b. poly(butyleneadipate) glycol (PBA) and c. chain extender, wherein the molar ratio of PBA and the diisocyanate is equal to or more than 0.8. By changing the molar composition of the components such as polyol and diisocyanate, physical and chemical property of the disclosed cone material in endodontic treatment can be adjusted.

6 Claims, No Drawings

CONE MATERIAL IN ENDODONTIC TREATMENT

CROSS REFERENCE TO RELATED APPLICATIONS

This application is a continuation in part of applicant's earlier application, Ser. No. 11/765,575, filed Jun. 20, 2007, now abandoned, which is related to U.S. patent application Ser. No. 11/765,591, filed Jun. 20, 2007, now abandoned.

BACKGROUND OF THE INVENTION

1. Field of the Invention

The present invention is generally related to a cone material in endodontic treatment, and more particularly to a thermoplastic polyurethane-based cone material in endodontic treatment.

2. Description of the Prior Art

The purpose of root canal treatment is to create an end result where the tissues that surround a tooth's root will maintain a healthy status despite the fact that the tooth's nerve has undergone degenerative changes. Root canal treatment occurs in three stages: First comes the diagnosis. Next comes the root canal itself, in which a dentist or an endodontist (a dentist who specializes in treating the inside of the tooth) removes the pulp (and thereby the infection), and cleans the inside of the tooth preparatory to filling it, sometimes applying antibiotics to thwart further infection. A temporary filling is placed at the crown opening. Finally, in a subsequent appointment, a crown is installed to seal the tooth and protect it from further damage or infection.

Root canal obturation involves inserting a filling cone into a root canal and cementing it therein to obturate the canal using a sealer. The common root canal filling cone material is made from gutta-percha or resilon. Lateral condensation and vertical condensation of warm or hot gutta-percha/resilon are methods be used in sealing root canals. After cementing a primary cone short of apex of the root canal, heat application is alternated with a series of smaller and smaller pluggers until the gutta-percha or resilon is moved to the apex.

The traditional root canal material is inert in nature and will not be absorbed or degraded by living tissue if the root canal is overfilled and extends beyond the apex. It has been a challenge for dentists to control the exact amount of the material within the border of the root canal to avoid overfilling. The cold core of the root canal material is not malleable so that it cannot be molded to the canal walls, resulting in poor adherence. In addition, when heated the root canal material cools to body temperature in the root, a uniform contraction takes place further reducing adherence to the root canal walls. Moreover, the filling is a polyisoprene rubber material in nature, which does not have the capability to bond to most dental materials, especially when the root canal sealer is a polymer-based material. Due to poor adherence and bonding, bacteria residential in the root canal can multiply or a leakage may result, causing bateria to enter the canal from the mouth, which can lead to the persistence of an infection or other complication. According to the above, it is important to develop a novel set of root canal material which has high biocompatibility, low volume contractive rate, better chemical-bonding ability with dentinal wall and the filling and high mechanical properties.

SUMMARY OF THE INVENTION

In light of the above background, the present invention provides a cone material in endodontic treatment.

One object of the present invention is to provide a cone material in endodontic treatment, comprising a thermoplastic polyurethane and a filler. The above-mentioned thermoplastic polyurethane is formed by reacting a. isophorone diisocyanate (IPDI) or hexamethylene diisocyanate (HDI) b. poly(butyleneadipate) glycol (PBA) of M.W.2000 and c. chain extender. By changing the molar composition of the components such as polyol and diisocyanate, physical and chemical property of the disclosed cone material in endodontic treatment can be adjusted. Moreover, the cone material in endodontic treatment can further comprise an antibiotic material to increase application performance. According to the above, the present invention does have the economic advantages for industrial applications.

DETAILED DESCRIPTION OF THE PREFERRED EMBODIMENTS

What is probed into the invention is a cone material in endodontic treatment. Detail descriptions of the structure and elements will be provided in the following in order to make the invention thoroughly understood. Obviously, the application of the invention is not confined to specific details familiar to those who are skilled in the art. On the other hand, the common structures and elements that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

One embodiment of the present invention discloses a cone material in endodontic treatment. The disclosed cone material comprises a thermoplastic polyurethane and a filler. The thermoplastic polyurethane and filler are well mixed in the cone material. The above-mentioned thermoplastic polyurethane is formed by a. isophorone diisocyanate (IPDI) or hexamethylene diisocyanate (HDI), b. poly(butyleneadipate) glycol (PBA) of M.W. 2000 and c. chain extender, wherein the molar ratio of PBA and the diisocyanate is equal to or more than 0.8. In addition, the above-mentioned filler is inorganic material and better comprises zinc oxide (ZnO), fluoroaluminosilicate glass, etc. The chain extender can be 1,4-Butanediol(1,4-BD).

Example 1

Thermal Properties of the Cone Material in Endodontic Treatment

This example compares the impact of polyol/diisocynanate/chain extender molar compositions on the thermal properties of the formed cone material. For each sample, the weight ratio of thermoplastic polyurethane and filler is less than 0.5. In this example, the chain extender is 1,4-butanediol (1,4-BD). The result of comparison is shown in Table 1.

TABLE 1

Thermal properties of the cone material in endodontic treatment

| poly-ol/diisocyanate/ chain extender (TPU: 30 wt % of total composite) | Melting point (° C.) | |
|---|---|---|
| | HDI as diisocyanate | IPDI as diisocyanate |
| 1/1.60/0.5 | 54.1 (Composite H1.) | 48.6 (Composite IP1.) |
| 1/1.36/0.3 | 53.9 (Composite H2.) | 48.0 (Composite IP2.) |
| 1/1.12/0.1 | 54.1 (Composite H3.) | 48.3 (Composite IP3.) |

(TPU: 30 wt % of total composite)

It is noted that the melting point of commercial gutta-percha is about 60.01° C., and the melting point of commercial resilon is about 60.01° C. (reference: A comparison of thermal properties between gutta-percha and a synthetic polymer based root canal filling material (Resilon). Journal of Endodontics, 2006 July; 32(7):683-6. Miner M R, Berzins D W, Bahcall J K.)

As shown in the result, when the molar ratio of polyol and diisocynanate is more than 0.6 (1/1.60>0.6), the sample utilizing Hexamethylene Diisocyanate (HDI) as diisocyanate to form the cone material has a melting point lower than 55° C. On the other hand, the sample utilizing Isophorone Diisocyanate (IPDI) as diisocyanate to form the cone material has a melting point lower than 48.6° C. There is no significant change on the melting point of the cone material when the molar ratio of polyol and diisocynanate increases (higher than 0.8 (1/1.12>0.8)). In both the HDI system and IPDI system, the melting point is lower than 55° C., which is also lower than that of commercial gutta-percha and resilon. In clinical root canal treatment, dentists usually have to conduct material into the root canal. For this purpose, the cone material is usually heated into liquid condition in advance. Therefore, the melting point of the cone materials cannot be too high. Accordingly, the present invention does have the economic advantages for industrial applications.

Example 2

Mechanical Properties of the Cone Material in Endodontic Treatment

This example compares the impact of polyol/diisocynanate/chain extender molar ratio on the thermal properties of the formed cone material. The weight ratios of the thermoplastic polyurethane and filler are lower than 0.5. In this example, the chain extender is 1,4-butanediol (1,4-BD). The result of comparison is shown in Table 2.

TABLE 2

Mechanical properties of the cone material in endodontic treatment

| Designations | TPU Composition (Polyol/ Diisocyanate/ Chain extender) | Mechanical Properties | |
|---|---|---|---|
| | | Tensile Strength (Mpa) | Yang's Modulus (Mpa) |
| Composite H1 | 1/1.60/0.5 | Not-available | Not-available |
| Composite H2 | 1/1.36/0.3 | Not-available | Not-available |
| Composite H3 | 1/1.12/0.1 | 21.8 ± 2.6 | 130.0 ± 18.3 |
| Composite IP1 | 1/1.60/0.5 | Not-available | Not-available |
| Composite IP2 | 1/1.36/0.3 | 0.8 ± 0.5 | 32.1 ± 13.4 |
| Composite IP3 | 1/1.12/0.1 | 15.8 ± 1.9 | 96.2 ± 17.7 |
| Gutta-percha | — | 5.98 ± 1.15(a) | 78.71 ± 23.41(a) |
| Resilon | — | 8.09 ± 2.30(a) | 86.58 ± 42.23(a) |

As shown in the table, tensile strength of commercial gutta-percha and resilon is generally less than 10 MPa, and Young's Modulus of gutta-percha and resilon is generally less than 90 MPa. In this example, when the molar ratio of polyol and diisocynanate is greater than 0.8 (polyol:diisocynanate=1:1.12), the sample utilizing IPDI as diisocyanate to form cone material has a tensile strength and Young's Modulus of 10 MPa (IP3; 15.8 MPa) and 90 MPa (IP3; 96.2 MPa), respectively. The sample utilizing HDI as diisocyanate to form cone material has a tensile strength and Young's Modulus of 20 MPa (H3; 21.8 MPa) and 100 MPa (H3; 130.0 MPa), respectively. The mechanical properties of root canal material determine the post-treatment tooth tightness and chewing ability, therefore the present invention has a great potential in the application of root canal material.

Furthermore, the above-mentioned cone material can further comprise an antibiotic material to increase its performance.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:

1. A cone material in endodontic treatment, comprising:
a thermoplastic polyurethane which is formed by (a) isophorone diisocyanate (IPDI) or hexamethylene diisocyanate (HDI), (b) poly(butyleneadipate) glycol (PBA), wherein the molecular weight of poly(butyleneadipate) glycol (PBA) is about 2000, and (c) chain extender, wherein the molar ratio of PBA to the diisocyanate is equal to or more than 0.8; and
a filler selected from the group consisting of zinc oxide (ZnO) and fluoroaluminosilicate glass;
wherein the tensile strength of the cone material is equal to or more than 10 MPa and the Young's Modulus of the cone material is equal to or more than 90 MPa.

2. The cone material according to claim 1, wherein the tensile strength of the cone material is equal to or more than 20 MPa.

3. The cone material according to claim 1, wherein the Young's Modulus of the cone material is equal to or more than 100 MPa.

4. The cone material according to claim 1, wherein the weight ratio of the thermoplastic polyurethane and the filler is equal to or less than 0.5.

5. The cone material according to claim 1, wherein the melting point of the cone material is equal to or lower than 55° C.

6. The cone material according to claim 1, wherein the cone material further comprises an antibiotic material.

* * * * *